(12) United States Patent
Imrich

(10) Patent No.: US 7,465,587 B2
(45) Date of Patent: Dec. 16, 2008

(54) DIAGNOSTIC ASSAY DEVICE

(75) Inventor: Michael Reece Imrich, Encinitas, CA (US)

(73) Assignee: Genzyme Corporation, Cambridge, MA (US)

( * ) Notice: Subject to any disclaimer, the term of this patent is extended or adjusted under 35 U.S.C. 154(b) by 412 days.

(21) Appl. No.: 11/004,370

(22) Filed: Dec. 3, 2004

(65) Prior Publication Data

US 2006/0121626 A1 Jun. 8, 2006

(51) Int. Cl.
*G01N 33/53* (2006.01)

(52) U.S. Cl. .................. 436/514; 435/287.7; 435/287.8; 435/287.9; 435/961; 436/518; 436/824; 436/810; 436/825; 436/529

(58) Field of Classification Search .................. 436/518, 436/528, 810, 825, 514, 824, 529; 435/287.7, 435/97, 287.8, 287.9, 961

See application file for complete search history.

(56) References Cited

U.S. PATENT DOCUMENTS

| | | | |
|---|---|---|---|
| 4,235,601 A | 11/1980 | Deutsch et al. | |
| 4,361,537 A | 11/1982 | Deutsch et al. | |
| 4,366,241 A | 12/1982 | Tom et al. | |
| 4,703,017 A | 10/1987 | Campbell et al. | |
| 4,790,979 A | 12/1988 | Terminiello et al. | |
| 4,855,240 A | 8/1989 | Rosenstein et al. | |
| 4,857,453 A | 8/1989 | Ullman et al. | |
| 4,861,711 A | 8/1989 | Friesen et al. | |
| 4,943,522 A | 7/1990 | Eisinger et al. | |
| 4,954,327 A | 9/1990 | Blount | |
| 4,954,452 A | 9/1990 | Yost et al. | |
| 4,965,047 A | 10/1990 | Hammond | |
| 5,073,484 A | 12/1991 | Swanson et al. | |
| 5,141,850 A | 8/1992 | Cole et al. | |
| 5,559,041 A * | 9/1996 | Kang et al. | 436/518 |
| 5,602,040 A | 2/1997 | May et al. | |
| 5,622,871 A | 4/1997 | May et al. | |
| 5,656,503 A | 8/1997 | May et al. | |
| 5,712,170 A | 1/1998 | Kouvonen et al. | |
| 5,712,172 A | 1/1998 | Huang et al. | |
| 5,714,389 A | 2/1998 | Charlton et al. | |
| 5,786,220 A | 7/1998 | Pronovost et al. | |
| 5,939,331 A | 8/1999 | Burd et al. | |
| 5,945,345 A * | 8/1999 | Blatt et al. | 436/518 |
| 5,989,921 A | 11/1999 | Charlton et al. | |
| 6,020,147 A | 2/2000 | Guire et al. | |
| 6,187,598 B1 | 2/2001 | May et al. | |
| 6,194,221 B1 | 2/2001 | Reng et al. | |
| 6,228,660 B1 | 5/2001 | May et al. | |
| 6,306,642 B1 | 10/2001 | Nelson et al. | |
| 6,352,862 B1 | 3/2002 | Davis et al. | |
| 6,485,982 B1 | 11/2002 | Charlton | |

(Continued)

FOREIGN PATENT DOCUMENTS

WO WO 97/06439 2/1997

(Continued)

*Primary Examiner*—Bao-Thuy L Nguyen
(74) *Attorney, Agent, or Firm*—Richard D. Allison; Thomas J. DesRosier

(57) ABSTRACT

This invention relates to assays for an analyte in a liquid sample such as a body fluid. More particularly, the invention relates to a method and apparatus for the detection of a ligand in a body fluid such as urine or blood, which includes an immobilization zone for interfering agents in a sample.

18 Claims, 6 Drawing Sheets

U.S. PATENT DOCUMENTS

| | | |
|---|---|---|
| 6,492,127 B2 * | 12/2002 | Goodell et al. ............... 435/7.1 |
| 6,528,323 B1 | 3/2003 | Thayer et al. |
| 6,534,320 B2 | 3/2003 | Ching et al. |
| RE38,430 E | 2/2004 | Rosenstein |
| 6,737,278 B1 * | 5/2004 | Carlsson et al. ............ 436/518 |
| 6,759,190 B2 | 7/2004 | Lin et al. |
| 2003/0049658 A1 * | 3/2003 | Smart et al. .................... 435/6 |
| 2004/0014094 A1 | 1/2004 | Lee et al. |
| 2004/0018556 A1 | 1/2004 | Cantor |

FOREIGN PATENT DOCUMENTS

| | | |
|---|---|---|
| WO | WO 98/22800 | 5/1998 |
| WO | WO 03/064046 | 8/2003 |

* cited by examiner

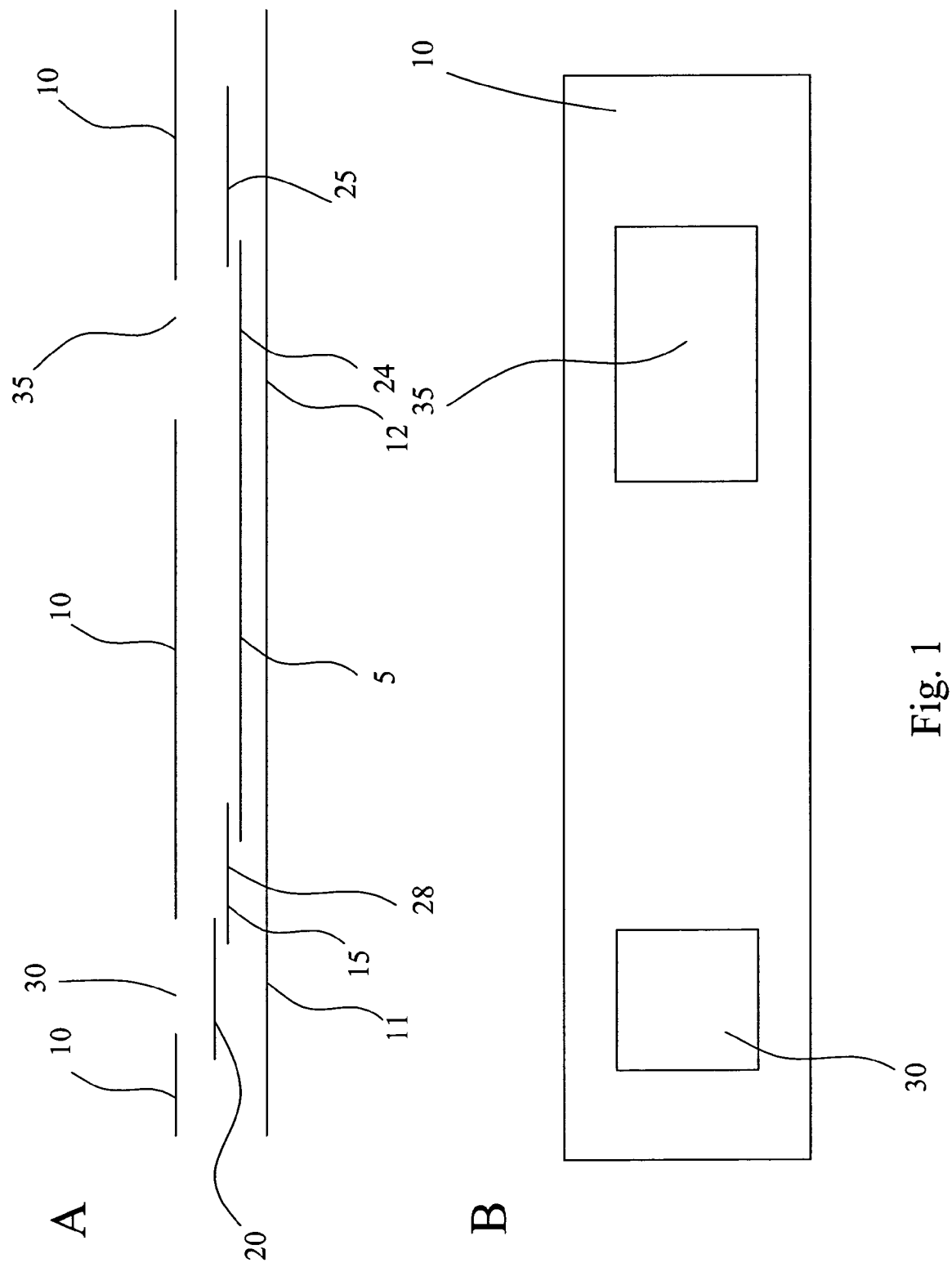

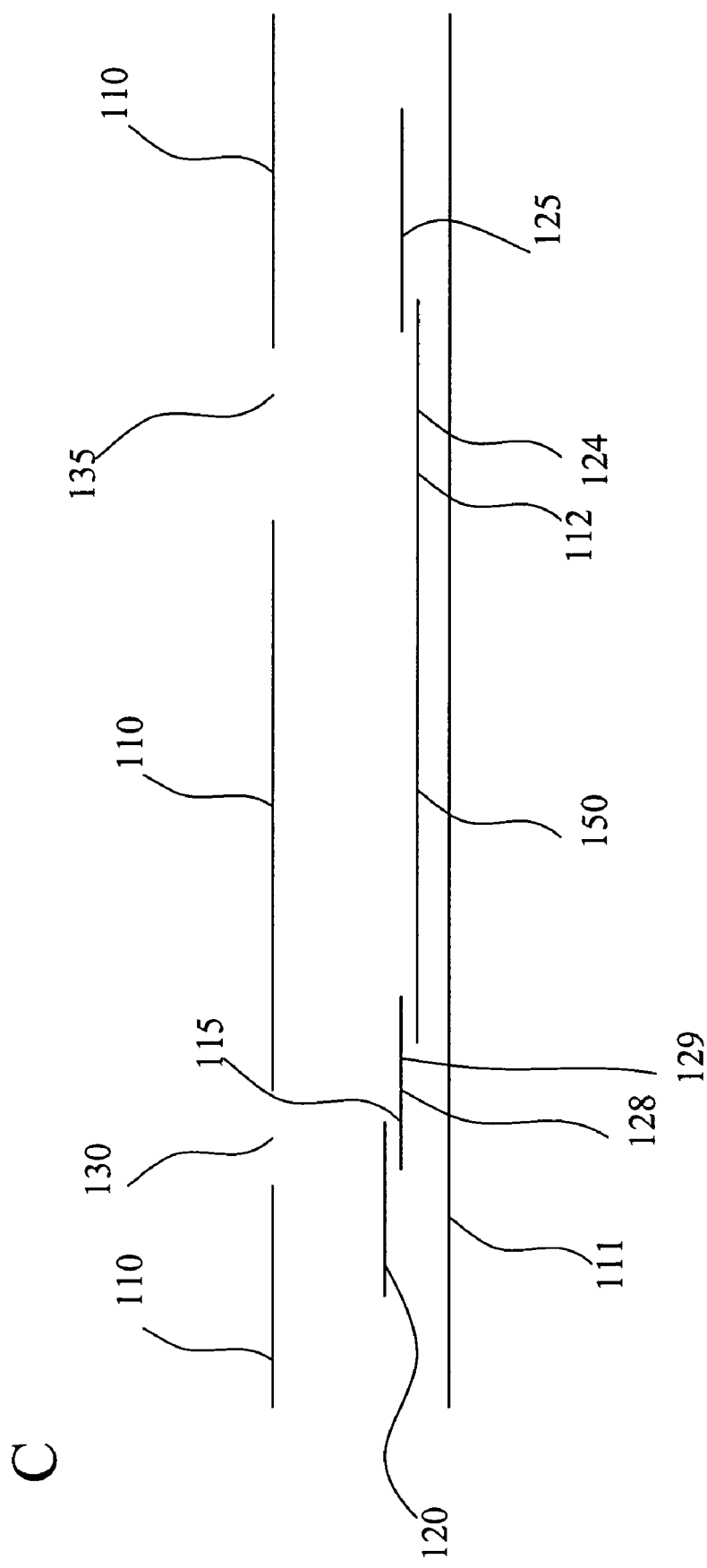

DIAGNOSTIC ASSAY DEVICE

BACKGROUND OF THE INVENTION

This invention relates to assays for analytes in a liquid sample such as a body fluid. More particularly, the invention relates to a method and apparatus for the detection of a ligand in a body fluid such as urine or blood.

Many types of ligand-receptor assays have been used to detect the presence of various substances in body fluids. These assays usually involve antigen antibody reactions or synthetic conjugates and are visualized by radioactive, enzymatic, fluorescent, or visually observable carbon or metal sol tags. In these assays, there is a receptor, e.g., an antibody, which is specific for the selected analyte and a means for detecting the presence, and often the amount, of the ligand-receptor reaction product.

The assays must be highly sensitive because of the often small concentration of the analyte of interest in the test fluid. False positives can also be troublesome, particularly when there are interfering substances in the body fluid that are able to produce a positive test result in the absence of analyte.

It is an object of this invention to provide a rapid, sensitive method for detecting analytes in body fluids. Another object is to provide an assay that has high sensitivity and fewer false positives than conventional assays.

BRIEF SUMMARY OF THE INVENTION

An assay device according to the invention comprises a sample receiving membrane which conducts lateral flow of a liquid sample, which is in lateral flow contact with an analyte detection membrane. The analyte detection membrane conducts lateral flow of the sample and comprises at least one interfering agent immobilization zone at a first situs, a conjugate forming membrane comprising a mobile labeling reagent at a labeling situs, and downstream from the immobilization zone an immobile capture reagent at a capture situs. The labeling reagent is capable of forming a complex with an analyte, the capture reagent is capable of binding an analyte-labeling reagent complex, and the interfering agent immobilization zone is capable of binding an interfering agent in the sample.

According to one embodiment, the interfering agent immobilization zone is an IgG antibody, an IgM antibody, or a portion thereof. The antibody or portion thereof may be from any mammalian species, e.g., from a mouse, goat, sheep, rat, human, rabbit, or cow antibody. Preferably, the interfering agent immobilization zone comprises a mouse or rat IgG because it is particularly effective, as many rapid test assay systems utilize at least one mouse monoclonal antibody that is subject to interference from heterophilic antibodies that bind to mouse immunoglobulins. Additionally, treatment with therapeutic agents derived from mouse monoclonal antibodies may evoke the production of Human Anti-Mouse Antibodies (HAMA) that will interfere with mouse antibodies used for analyte detection.

According to another embodiment, the interfering agent immobilization zone may be located between the sample receiving membrane and the mobile labeling situs. Alternately, the interfering agent immobilization zone may be located between the capture reagent and the labeling situs, or in the sample receiving membrane. In a related embodiment, the assay device may have a plurality of interfering agent immobilization zones located for example, located between the sample receiving membrane and the mobile labeling situs and another between the labeling situs and the capture situs.

Preferably, the back of the sample receiving membrane and the analyte detection membrane are laminated with a semi-rigid material. The semi-rigid material may be at least 0.005 inches thick to produce a device with adequate mechanical strength in the absence of a plastic casing. In a related embodiment, the sample receiving membrane and the analyte detection membrane are enclosed in a housing. The housing, may have a sample application aperture and an observation window positioned to display the immobile capture situs and control situs.

In a further embodiment, the device further comprises an absorbent sink in lateral flow contact with the analyte detection membrane.

In yet another embodiment, the device further comprises a control reagent immobilized at a control situs.

The analytes assayed by the devices and methods of the invention include, proteins, peptides, small molecules, antibodies, nucleic acids, viruses or virus particles, human chorionic gonadotrophin (hCG), luteinizing hormone (LH), estrone-3-glucoronide (E-3-G), pregnanediol-3-glucoronide (P-3-G), insulin, glucagon, relaxin, thyrotropin, somatotropin, gonadotropin, follicle-stimulating hormone, gastrin, bradykinin, vasopressin, polysaccharides, estrone, estradiol, cortisol, testosterone, progesterone, chenodeoxycholic acid, digoxin, cholic acid, digitoxin, deoxycholic acid, lithocholic acids; vitamins, thyroxine, triiodothyronine, histamine, serotorin, prostaglandins, drugs and metabolites thereof, ferritin, and CEA.

Interfering agents immobilized in the immobilization zone by the devices of the invention include, antibodies and analyte mimics.

In a further aspect, an assay device for detection of the presence or absence of an analyte in a sample comprises a membrane comprising, a sample receiving zone which conducts flow of a liquid sample, in flow contact with an analyte detection membrane which conducts flow of the sample comprising at least one interfering agent immobilization zone at a first situs, a conjugate forming membrane comprising a mobile labeling reagent at a labeling situs, and an immobile capture reagent at a capture situs, wherein the labeling reagent is capable of forming a complex with an analyte, the capture reagent is capable of binding an analyte-labeling reagent complex, and the interfering agent immobilization zone is capable of binding an interfering agent in the sample. A backing is laminated to a bottom surface of the sample receiving membrane and the analyte detection membrane, wherein the backing comprising semi-rigid material of at least 0.005 inches thick to produce a device with adequate mechanical strength in the absence of a plastic casing. Although the preferred arrangement of the present invention provides for the lateral flow of the liquid sample through the first situs, labeling situs and capture situs, it is anticipated that one or more of the respective situs may be arranged to overlap or are arranged in horizontal relationship with respect to each other.

According to a method aspect, a method of detecting the presence of an analyte in a sample comprises applying a sample to an assay device, wherein the assay device comprises a sample receiving membrane which conducts lateral flow of a liquid sample in lateral flow contact with an analyte detection membrane. The analyte detection membrane conducts lateral flow of the sample, wherein the analyte detection membrane comprises at least one interfering agent immobilization zone at a discrete first situs, a conjugate forming membrane comprising a mobile labeling reagent at a discrete labeling situs, and an immobile capture reagent at a discrete capture situs. The labeling reagent is capable of forming a complex with the analyte, the capture reagent is capable of binding the analyte-labeling reagent complex, and the interfering agent immobilization zone is capable of binding an interfering agent in the sample. The liquid sample laterally flows from said sample receiving membrane to the analyte detection membrane, and mixes with the mobile labeling reagent to move the mobile labeling reagent toward the control situs. A result is observed, wherein the accumulation of particles or other label produces an indicative signal of the presence of the analyte in the sample.

Another aspect of the invention is a kit comprising an assay device as described above and instructions for use.

Other embodiments of the invention are disclosed infra.

BRIEF DESCRIPTION OF THE DRAWINGS

FIGS. 1A, 1B, and 1C depict schematics of a device according to the invention.

DETAILED DESCRIPTION OF THE INVENTION

Figure 2:
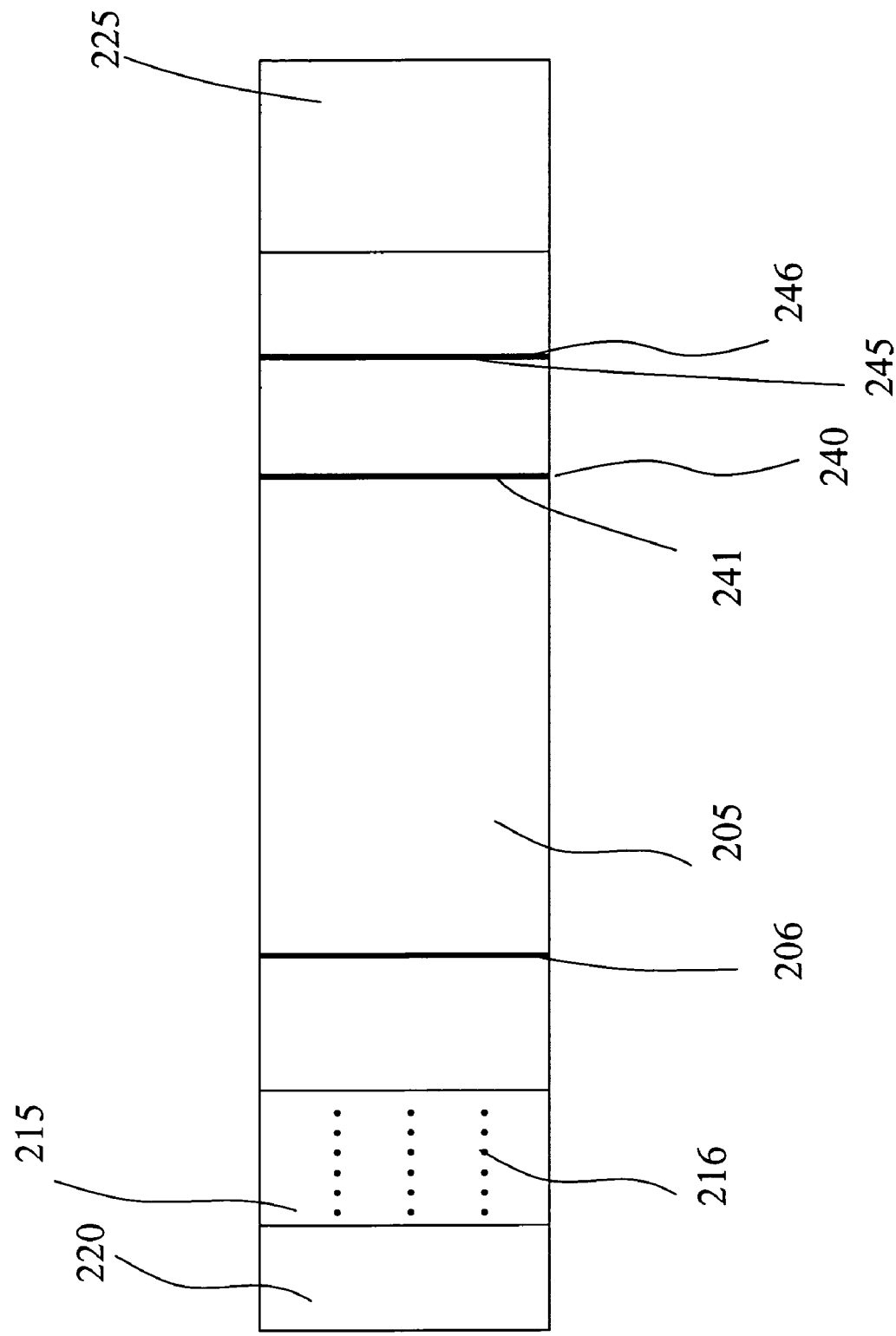
FIG. 2 depicts a top view of a device according to the invention.

Disclosed herein is an assay device to determine the presence or absence of an analyte in a sample. Further disclosed herein are methods for determining the presence or absence of an analyte in a sample. The devices and methods of this invention include an interfering agent immobilization zone that reduces the occurrence of false positive test results.

Broadly, the devices and methods of the invention can be used to detect any analyte that may be assayed using known immunoassay procedures, or known to be detectable by such procedures, using polyclonal or monoclonal antibodies or other proteins comprising binding sites for analytes. Various specific assay protocols, reagents, and analytes useful in the practice of the invention are known, for example, see U.S. Pat. No. 4,313,734, and U.S. Pat. No. 4,366,241.

As used herein, the term, "analyte" is intended to refer to any component of a sample (e.g., molecule, compound, or aggregate thereof) to be detected and optionally quantitatively determined by an assay device. Examples of analytes include proteins, such as hormones and other secreted proteins, enzymes, and cell surface proteins; glycoproteins; peptides; small molecules; polysaccharides; antibodies (including monoclonal or polyclonal Ab and portions thereof); nucleic acids; drugs; toxins; viruses or virus particles; portions of a cell wall; and other compounds possessing epitopes. Sandwich assays, for example, may be performed for analytes such as human chorionic gonadotrophin (hCG), luteinizing hormone (LH), and infectious disease agents, whereas competition assays, for example, may be carried out for analytes such as estrone-3-glucoronide (E-3-G) and pregnanediol-3-glucoronide (P-3-G). Also included as suitable analytes are hormones such as insulin, glucagon, relaxin, thyrotropin, somatotropin, gonadotropin, follicle-stimulating hormone, gastrin, bradykinin, vasopressin, and various releasing factors. A wide range of antigenic polysaccharides can also be determined such as those from *Chlamydia*, *Neisseria* gonorrheae, *Pasteurella* pestis, *Shigella* dysentereae, and certain fungi such as *Mycosporum* and *Aspergillus*. Another major group comprises oligonucleotiae sequences, which react specifically with other oligonucleotides or protein targets. An extensive list of soluble analytes determinable in the method of the invention is found in U.S. Pat. No. 3,996,345, to Syva Co., which is incorporated herein by reference. Other representatives of analytes determinable by the method of the present invention include steroids such as estrone, estradiol, cortisol, testosterone, progesterone, chenodeoxycholic acid, digoxin, cholic acid, digitoxin, deoxycholic acid, lithocholic acids and the ester and amide derivatives thereof; vitamins such as B-12, folic acid, thyroxine, triiodothyronine, histamine, serotorin, prostaqlandins such as PGE, PGF, PGA; antiasthmatic drugs such as theophylline, antineoplastic drugs such as doxorubicin and methotrexate; antiarrhythmic drugs such as disopyramide, lidocaine, procainamide, propranolol, quinidine, N-acetylprocainamide; anticonvulsant drugs such as phenobarbital, phenytoin, primidone, valproic acid, carbamazepine and ethosuximide; antibiotics such as penicillins, cephalosporins, erythromycin, vancomycin, gentamicin, amikacin, chloramphenicol, streptomycin and tobramycin; antiarthritic drugs such as salicylate; antidepressant drugs including tricyclics such as nortriptyline, amitriptyline, imipramine and desipramine; and the like as well as the metabolites thereof.

Additional analytes that may be determined by the methods of the present invention include drugs of abuse such as morphine, heroin, hydromophone, oxymorphone, metapon, codeine, hydrocodone, dihydrocodiene, dihydrohydroxy codeinone, pholcodine, dextromethorphan, phenazocine and deonin and their metabolities. Higher molecular weight analytes such as aminoacids, polypeptides, and proteins such as, TSH, ferritin, CEA and C-reactive protein may also be determined by the methods of the present invention.

It may be desired to assay two or more different analytes using the same device. In such instances, it may be desirable to employ different detectable markers on the same test strip where each detectable marker detects a different analyte. For example, different detectable markers may be attached to different mobile labeling reagents. The different detectable markers may be different fluorescent agents, which fluoresce at different wavelengths or differently colored dyes or particles. When detecting two or more different analytes using the same device, separate test detection or capture zones may optionally be formed on the test strip for each analyte to be detected. The same detectable marker may be used for all of the analytes. Alternatively, different detectable markers, as described above, may be used for the different analytes to prevent one capture zone being confused with another.

The term "sample" as used herein refers to any biological sample that could contain an analyte for detection. Preferably the biological sample is in liquid form or can be changed into a liquid form. Preferably, the sample is a urine sample, or material extracted from a swab of throat tissue. Samples include blood, serum, nasal, urine, sweat, plasma, semen, cerebrospinal fluid, tears, pus, amniotic fluid, saliva, lung aspirate, gastrointestinal contents, vaginal discharge, urethral discharge, chorionic villi specimens, skin epithelials, genitalia epithelials, gum epithelials, throat epithelials, hair, and sputum.

Sample volumes can range from between about 0.05 mL to about 0.5 mL of sample applied to the assay device. Alternately, enough sample should be applied to the assay device to ensure proper sample flow through the device, and to ensure proper flow of analyte (if present) through the device. Enough sample to ensure the mobility of the mobile labeling reagent is preferable. The amount of sample may depend, in part, on the absorbency of the sample receiving membrane, the absorbent sink, the length of the membranes, and width of the membranes, or the temperature of the device at the time of use and whether or not a reagent is added to the sample prior to the application of the sample to the sample receiving member.

As used herein, "interfering agent" refers to an agent in a sample that is capable of binding to the mobile labeling reagent and producing a false positive or false negative result when the sample is applied to an assay device. The interfering agent may be a heterophilic antibody, a lectin, a monoclonal antibody, a polyclonal antibody, or an analyte mimic. An analyte mimic is any substance or molecule other than the analyte that has an epitope recognized by the mobile labeling reagent or is otherwise non-specifically recognized by the mobile labeling reagent.

As used herein, "interfering agent immobilization zone" refers to a reagent, for example a non-immune mouse IgG, which is immobilized on one or more of the membranes of a device according to the invention. The immobilization zone is capable of binding to interfering agents and/or interfering agents that are bound to the mobile labeling reagent. The interfering agent immobilization zone may be located in the sample receiving zone and/or on the analyte detection membrane prior to the capture reagent. A device may have one or more lines or regions of immobilized interfering agent immobilization zones. The immobilization zones may be immobilized by techniques known in the art and as discussed further infra. The interfering agent immobilization zones are capable of binding to a plurality of interfering agents.

In addition to the creation of the interfering agent immobilization zone by application of the immobilization reagent to a membrane capable of binding proteins, other means of achieving the creation of an immobilization zone are possible. For example, in cases where the sample receiving membrane or mobile label reagent zone are composed of cellulosic materials, the immobilization zone can be formed during a pre-treatment step of the cellulose. Activation of paper with CNBr and subsequent covalent coupling with IgG has been described in "Laboratory Techniques in Biochemistry and Molecular Biology," Tijssen, Vol. 15, Practice and Theory of Enzyme immunoassays, chapter 13, The Immobilization of Immunoreactants on Solid Phases, pp. 319. An alternative to CNBr activation can be achieved by a modification of the protocol described in the aforementioned reference for activating Sepharose with $NaIO_4$. The use of Sodium Periodate poses less of a health risk than the use of the poisonous CNBr. After the cellulosic material is coupled with the immobilization reagent, the resulting material can be dried or lyophilized. The dried material can then serve as the base matrix for subsequent use as a sample receiving or mobile label reagent zone in the construction of an assay device. In this model, the base matrix is composed of covalently bound immobilization reagent, which can bind interfering substances. The wicking properties of the cellulose matrix are preserved, allowing it to be a suitable material for facilitating sample wicking and mobile labeling reagent release.

The sample receiving membrane and the analyte detection membrane may be made of any substance having sufficient porosity to allow capillary action of fluid along its surface and/or through its interior. The porous material of either the sample receiving membrane or the analyte detection membrane should have sufficient porosity to allow movement of antibody- or antigen-coated particles. The porous material of either the sample receiving membrane or the analyte detection membrane should also be wettable by the fluid used in the sample, which contains the analyte to be detected. Hydrophobicity of a porous material, sometimes referred to herein as a membrane, can be altered to render the membrane hydrophilic for use with aqueous fluid, by processes such as those described in U.S. Pat. No. 4,340,482, or U.S. Pat. No. 4,618,533. Examples of substances which can be used to form a porous material of either the sample receiving membrane or the analyte detection membrane include cellulose, nitrocellulose, cellulose acetate, glass fiber, nylon, polyelectrolyte ion exchange membrane, acrylic copolymer/nylon, and polyethersulfone. In a preferred embodiment, the porous material of either or both the sample receiving membrane and/or the analyte detection membrane are made of nitrocellulose. One skilled in the art will be aware of other porous materials that allow lateral flow. The term "lateral flow" refers to liquid flow in which all of the dissolved of dispersed components of the liquid are carried, preferably, at substantially equal rates and with relatively unimpaired flow laterally through the material, as opposed to preferential retention of one or more components as would occur. Nitrocellulose has the advantage that proteinaceous reagents, such as an antibody, in the capture situs can be immobilized firmly without prior chemical treatment. If the membrane comprises paper, for example, the immobilization of an antibody in the second zone may be performed by chemical coupling using, for example, CNBr, carbonyldiimidazole, Sodium Periodate, or tresyl chloride.

Preferably the nitrocellulose sheet has a pore size of at least about 1 micron, even more preferably of greater than about 5 microns, and yet more preferably about 8-12 microns. Very suitable nitrocellulose sheet having a nominal pore size of up to approximately 12 microns, is available commercially from Sartorius GmbH (Goettingen, Germany).

Optionally, the nitrocellulose or other sample flow sheets may be "backed," e.g. with plastics sheet, to increase its handling strength. This can be manufactured easily by forming a thin layer of nitrocellulose on a sheet of backing material. The actual pore size of the nitrocellulose when backed in this manner will tend to be lower than that of the corresponding unbacked material. Alternatively, a pre-formed sheet of nitrocellulose can be tightly sandwiched between two supporting sheets of solid material, e.g. plastics sheets.

The term "mobile" as referred to herein means diffusively or non-diffusively attached, or impregnated.

Preferably the membranes are in the form of a strip or sheet to which during manufacture of the device, one or more reagents can be applied in spatially distinct zones. During use, the liquid sample is allowed to permeate through the sheet or strip from one side or end to another. Reagents that may be applied to the membranes of the invention include the capture reagent, the interfering agent immobilization zone, the control reagent, and the mobile labeling reagent. The reagents may be diffusively or non-diffusively bound to the membranes.

If desired, a device according to the invention can incorporate two or more discrete bodies of membrane, e.g. separate strips or sheets, some carrying mobile and/or immobilized reagents. These discrete bodies can be arranged in parallel, for example, such that a single application of liquid sample to the device initiates sample flow in the discrete bodies simultaneously. The separate analytical results that can be determined in this way can be used as control results, or if different reagents are used on the different carriers, the simultaneous determination of a plurality of analytes in a single sample can be made. Alternatively, multiple samples can be applied individually to an array of carriers and analyzed simultaneously.

Following the application of a reagent to the capture situs and the interfering agent immobilization zone reagent, the remainder of the membrane may be treated to block any remaining binding sites elsewhere. Blocking can be achieved by treatment with protein (e.g. bovine serum albumin or milk protein), or with polyvinylalcohol or ethanolamine, or any combination of these agents, for example. Between these process steps the membrane may be dried.

It is preferable that the flow rate of an aqueous sample through the membrane be such that in the untreated material, aqueous liquid migrates at a rate of 1.8 cm in approximately 1 minute, but slower or faster flow rates can be used if desired.

The spatial separation between the sample application membrane and the capture situs, and the flow rate characteristics of the membrane, can be selected to allow adequate reaction times during which the necessary specific binding can occur. Further control over these parameters can be achieved by the incorporation of viscosity modifiers (e.g. sugars and modified celluloses) in the sample to slow down the reagent migration.

Reagents can be applied to the membrane materials in a variety of ways. Various "printing" techniques are suitable for application of liquid reagents to the membranes, e.g. microsyringes, pens using metered pumps, direct printing, ink-jet printing, air-brush, and contact (or filament) methods, and any of these techniques can be used in the present context. To facilitate manufacture, the membrane can be treated with the reagents and then subdivided into smaller portions (e.g. small narrow strips each embodying the required reagent-containing zones) to provide a plurality of identical carrier units.

As used herein, the term "sample receiving membrane," "sample receiving zone, and sample receiving region" are used interchangeably and refer to the portion of the assay device that may be in direct contact with the liquid sample, e.g., it receives the sample to be tested for the analyte in question. The sample can then migrate, for example, by lateral flow from the sample receiving membrane towards the capture situs and optionally to the absorbent sink. Preferably the sample receiving membrane is near one edge of the assay device. The sample receiving membrane is in flow contact with either a labeling reagent membrane or the analyte detection membrane. This could be an overlap, end-to-end connection, stacked or the like. The sample receiving membrane may be impregnated with buffer to neutralize reagents in the sample during the lateral flow immunoassay. The analyte in the sample should be capable of migrating, through lateral flow, with the liquid sample.

The sample receiving membrane can be made from any bibulous, porous or fibrous material capable of absorbing liquid rapidly. The porosity of the material can be unidirectional (e.g., with pores or fibers running wholly or predominantly parallel to an axis of the membrane) or multidirectional (omnidirectional, so that the membrane has an amorphous sponge-like structure). Porous plastics material, such as polypropylene, polyethylene (preferably of very high molecular weight), polyvinylidene fluoride, ethylene vinylacetate, acrylonitrile and polytetrafluoro-ethylene can be used. It can be advantageous to pre-treat the membrane with a surface-active agent during manufacture, as this can reduce any inherent hydrophobicity in the membrane and therefore enhance its ability to take up and deliver a moist sample rapidly and efficiently. The sample receiving membranes can also be made from paper or other cellulosic materials, such as nitro-cellulose. Materials that are now used in the nibs of so-called fiber tipped pens are particularly suitable and such materials can be shaped or extruded in a variety of lengths and cross-sections appropriate in the context of the invention. Preferably the material comprising the porous receiving membrane should be chosen such that the membrane can be saturated with aqueous liquid within a matter of seconds. Preferably the material remains robust when moist. The liquid must thereafter permeate freely from the sample receiving membrane into the analyte detection membrane. Suitable materials also include cotton, cellulose, mixed fibers, glass fiber and the like. For example, paper such as 470 and 740-E from Schleicher and Schuell, Keen, N.H., or D28 from Whatman, Fairfield, N.J., can be selected for its high fluid absorption and wicking speed. A more porous material such as glass fiber #66078 from Gelman Sciences, Ann Arbor, Mich., or "POREX" from Porex Technologies, Fairburn, Ga., is suitable for impregnating labeled particles.

The absorption capacity of the sample receiving membrane may be sufficiently large to absorb the fluids that are delivered to the test strip or membrane. The sample-receiving zone serves to begin the flow of analyte-containing sample, and typically will be constructed of a material that exhibits low analyte retention. The sample-receiving zone may also function as a mechanical immobilization zone, entrapping any undesirable particulates present in the sample.

Devices of the invention may have an absorbent sink in flow contact with at least the analyte detection membrane. The absorbent sink may be formed of any absorbent substance. Examples of substances that may be used include cellulose, cellulose nitrate, cellulose acetate, glass fiber, nylon, polyelectrolyte ion exchange membrane, acrylic copolymer/nylon, Whatman 3MM, polyethersulfone, 470 and 740-E from Schleicher and Schuell, Keen, N.H., or D28 from Whatman, Fairfield, N.J., can be selected for their high fluid absorption and wicking speed.

The sample receiving membrane, the absorbent sink, the conjugate forming membrane all have a bottom or back surface. The bottom surface may have an adhesive applied to it so that it may be backed by a semi-rigid material to add strength to the membrane.

The absorbent sink may be made of the same material as the sample receiving membrane or it may be made of a different material. The sink, the sample receiving membrane and the analyte detection membrane may be made of the same material, or they may each be made of different materials.

"Labeling reagent," as used herein refers to a detectable marker, for example, a colored particle. Examples of particles that may be used include, but are not limited to, colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; carbon black particles, colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads.

One preferred class of particles is colloidal gold particles. Colloidal gold particles may be made by any conventional method, such as the methods outlined in G. Frens, 1973 Nature Physical Science, 241:20 (1973). Alternative methods may be described in U.S. Pat. Nos. 5,578,577, 5,141,850; 4,775,636; 4,853,335; 4,859,612; 5,079,172; 5,202,267; 5,514,602; 5,616,467; 5,681,775.

Another preferred class of particles, are carbon particles, for example carbon black particles. The carbon label may be attached by methods well known to those skilled in the art, including the methods described in U.S. Pat. Nos. 5,252,496 and 5,559,041 to Princeton Biomeditech Corporation (Monmouth, N.J.), and U.S. Pat. Nos. 5,529,901; 5,294,370; 5,348, 891 and 5,641,689 to ATO.

The selection of particle size may be influenced by such factors as stability of bulk sol reagent and its conjugates, efficiency and completeness of release of particles from conjugate pad, speed and completeness of the reaction. Also, the fact that particle surface area may influence steric hindrance between bound moieties may be considered. Particle size may also be selected based on the porosity of the porous material of either the sample receiving membrane or the analyte detection membrane. The particles are preferably sufficiently small to diffuse along the membrane by capillary action of the conjugate buffer.

Metal sols and other types of colored particles useful as marker substances in immunoassay procedures are also known per se. See, for example, U.S. Pat. No. 4,313,734, Feb. 2, 1982, to Leuvering, the disclosure of which is incorporated herein by reference. For details and engineering principles involved in the synthesis of colored particle conjugates see Horisberger, Evaluation of Colloidal Gold as a Cytochromic Marker for Transmission and scanning Electron Microscopy, Biol. Cellulaire, 36, 253-258 (1979); Leuvering et al, Sol Particle Immunoassay, J. Immunoassay 1 (1), 77-91 (1980), and Frens, Controlled Nucleation for the Regulation of the Particle Size in Monodisperse Gold Suspensions, Nature, Physical Science, 241, pp. 20-22 (1973).

The number of labeling particles present in the porous material of either the sample receiving membrane and/or the analyte detection membrane or test strip may vary, depending on the size and composition of the particles, the composition of the test strip and porous material of either the sample receiving membrane or the analyte detection membrane, and the level of sensitivity of the assay. The number of particles typically ranges between about $1\times10^9$ and about $1\times10^{13}$ particles, although fewer than about $1\times10^9$ particles may be used. In a preferred embodiment, the number of particles is about $1\times10^{11}$ particles.

Particles may be labeled to facilitate detection. Examples of labels include, but are not limited to, luminescent labels; colorimetric labels, such as dyes; fluorescent labels; or chemical labels, such as electroactive agents (e.g., ferrocyanide); enzymes; radioactive labels; or radio frequency labels.

Indirect labels, such as enzymes, e.g. alkaline phosphatase and horseradish peroxidase, can be used but these usually require the addition of one or more developing reagents such as substrates before a visible signal can be detected. Such additional reagents can be incorporated in the membranes, such that they dissolve or disperse in the aqueous liquid sample. Alternatively, the developing reagents can be added to the sample before contact with the membranes or the membranes can be exposed to the developing reagents after the binding reaction has taken place. Coupling of the label to the mobile labeling reagent may be by covalent bonding, or by hydrophobic bonding. Such techniques are commonplace in the art. In a preferred embodiment, where the label is a direct label such as a colored latex particle, hydrophobic bonding is preferred.

The presence or intensity of the signal from the label which becomes bound in the capture situs can provide a qualitative or quantitative measurement of analyte in the sample. A plurality of detection or capture zones arranged in series on the membrane, through which the aqueous liquid sample can pass progressively, can also be used to provide a quantitative measurement of the analyte, or can be loaded individually with different specific binding agents to provide a multi-analyte test.

The reagents that are mobile or releasably bound are capable of dispersing with the liquid sample upon rehydration and are carried by the liquid sample in the lateral flow. The terms "immobile" or "immobilized" as used herein refer to reagents which are attached to the support such that lateral flow of the liquid sample does not affect the placement of the immobile particle in the discrete membrane of the porous material. Such attachment can be through covalent, ionic or hydrophobic means. Those skilled in the art will be aware of means of attachment to immobilize various particles. The interfering agent immobilization zone contains immobilized reagent, e.g., pre-immune mouse IgG.

The term "mobile labeling reagent" refers to a suitable reagent labeled with a particle described above. The mobile labeling reagent may be a protein or molecule which recognizes or binds to the analyte in question, and which is conjugated or attached to a substance or particle capable of producing a signal that is detectable by visual or instrumental means. The attachment to the substance or particle capable of producing a signal may be chemical, covalent or noncovalent, ionic or non-ionic. The particle or molecule recognizing the analyte can be either natural or non-natural, preferably monoclonal or polyclonal antibody or a lectin.

Mobile labeling reagents may be, for example, a monoclonal or polyclonal antibody to either the α or the β-epitope of hCG, Flu A or Flu B antibodies, or a polyclonal or monoclonal antibody to the carbohydrate antigen of *Streptococcus* Group A. Other examples include, antibodies specific for *Trichomonas vaginalis, Giardia lambia*, and *Cryptosporidium parvum*. It is well known in the art that the carbohydrate antigen of Group A *Streptococcus* contains a repeated epitope. Thus, a sandwich complex can be formed even if the indicator capture reagent and the indicator labeling reagent each contain an antibody to the same epitope of Strep A.

The term "labeling reagent membrane" refers to a membrane which contains indicator labeling reagent. The labeling reagent membrane may also contain control labeling reagent. The separate labeling reagent membrane is preferably made of a mixture of cellulose and polyester, or other porous material.

The term "discrete situs," "capture situs" or "control situs" as used herein refer to a defined area in which either the mobile labeling reagents, the capture reagent, or the control reagent are impregnated or immobilized to the membrane. The situs of the control capture reagent or the capture reagent for the analyte provide a discrete visible signal in a desired geometric shape from which to view the results of the test. For example, if the one mobile labeling reagent is analyte bound to anti-analyte conjugated to Blue latex label, then a discrete blue signal will appear at the discrete capture situs if the indicator capture reagent binds and immobilizes the analyte-labeling reagent complex. If the control labeling reagent is BSA conjugated to a label such as colored latex or gold sol, then a discrete signal will form at the discrete control situs if the control capture reagent has immobilized the BSA-control labeling reagent.

Control reagents according to the invention may be used to perform a variety of control functions. For example, control reagents may be used to ensure that the assay device is in good working order, they may be used to determine whether the sample has wicked through the membranes properly, they may function to indicate when the assay may be read, e.g., signal the end of the reaction, they may function as internal standards and allow analyte measurement results to be compared between different test strips, and can be useful in demonstrating that the indicator labeling reagent is intact which can provide an indication of the ongoing functionality of the indicator labeling reagent.

A wide variety of reagents are known in the art that may be used as a control reagent. For example, a naturally occurring or engineered protein may be used to bind unbound mobile labeling reagent. The control reagent may also be one member of a pair of a receptor-ligand pair. Additionally, at least one membrane of the control reagent may be an antigen, another organic molecule, or a hapten conjugated to a protein non-specific for the analyte of interest. Descriptions of other suitable control reagents may be found in U.S. Pat. No. 5,096,837, and include IgG, goat anti-mouse antibodies, other immunoglobulins, bovine serum albumin (BSA), other albumins, casein, and globulin or portions thereof. As a further alternative, a control zone could contain immobilized analyte which will react with excess labeled reagent from the first zone. As one purpose of the control zone is to indicate to the user that the test has been completed, the control zone should be located downstream from the capture situs in which the desired test result is recorded. A positive control indicator therefore tells the user that the sample has permeated the required distance through the test device.

Desirable characteristics for control reagents include, but are not limited to stability in bulk, non-specificity for analyte of interest, reproducibility and predictability of performance in test, molecular size, avidity of binding for each other, ability to bind to a membrane, binding availability upon biding to membrane, and immobilization potential.

The devices of the present invention also may include a procedural control which comprises visible moieties that do not contain the specific binding agent or analyte competitor and that are also carried through to a control area of the capture zone by the liquid flow. These visible moieties are coupled to a control reagent which binds to a specific capture partner and can then be captured in a separate procedural control portion of the capture zone to verify that the flow of liquid is as expected. The visible moieties used in the procedural control may be the same or different color than those used for the test moieties. If different colors are used, ease of reading the results is enhanced. In one preferred embodiment, the procedural control may include a signal that become visible when the sample wicks through the portion of the membrane in the location of the signal. The procedural control may be a line drawn on the housing beneath the membrane, it may be a line on the backing beneath the test strip, or it may be a reagent adhered to, in, on, or within the membrane that becomes visible upon contact with a sample. Alternatively, the control zone can contain an anhydrous reagent that, when moistened, produces a color change or color formation, e.g. anhydrous copper sulphate which will turn blue when moistened by an aqueous sample.

In a preferred embodiment, the membranes include more than one control zone or situs and may be used to create a calibration curve against which a wide variety of analyte measurement results may be compared. Having the test strip possess more than one control zone allows lateral flow assays to have a wider dynamic range than conventional lateral flow assays. In preferred embodiments, test strips with 2, 3 or more control zones are used with a relative scale methodology, discussed further below, that permits mapping of amounts of control binding pairs detected onto the same scale on which amounts of analyte detected are reported.

The devices of the invention may also be used to determine quantitatively the amount of analyte in a sample. Once the amount of detectable markers has been measured in each test zone, these measurements may be used to detect and preferably quantify the amount of analyte present, preferably by also calibrating the test device using the amounts of detectable markers in one or more control zones.

Examples of detection techniques useful in the invention include seeing a visible signal with the eye and optical methods (light scattering, simple reflectance, luminometer or photomultiplier tube); radioactivity; electrical conductivity; dielectric capacitance; and/or electrochemical detection of released electroactive agents.

In certain preferred embodiments, the mobile labeling reagent and the immobile capture reagent are antibodies specific for the analyte. Preferably, the mobile labeling regent and the immobile capture reagent recognize and bind to, for example, different portions of the analyte or to different subunits of the analyte. Antibodies may be polyclonal or monoclonal or fractions thereof. Polyclonal antisera and indeed monoclonal antibodies or fractions thereof having specific binding properties and high affinity for virtually any antigenic substance are known and commercially available or can be produced from stable cell lines using well known cell fusion and screening techniques. The literature is replete with protein immobilization protocols. See, for example, "Laboratory Techniques in Biochemistry and Molecular Biology," Tijssen, Vol. 15, Practice and Theory of Enzyme immunoassays, chapter 13, The Imobilization of Immunoreactants on Solid Phases, pp. 297-328, and the references cited therein.

Examples of antibodies useful in the methods and device of the invention include the anti-β-hCG antibody, anti-α-hCG antibody, anti-flu A, anti-flu B, anti-strep A antibody, anti-Trichomonas antibody, anti-*Giardia* antibody, and anti-*Cryptosporidium* antibody. A monoclonal anti-β-hCG antibody can be obtained from commercial sources, and formerly from Medix Biochemica (Kauniainen, Finland). An affinity purified polyclonal anti-α-hCG antibody (rabbit) can be purchased from Bioreclamation (East Meadow, N.Y.) or and other sources. As is discussed below, the mobile labeling reagent recognizes the β-hCG subunit, the capture reagent recognizes the α-hCG subunit, and the control agent recognizes the anti-β-hCG antibody or fragment thereof not captured by the capture reagent. Antibodies used for the detection of Influenza (Flu) A or B are typically targeted toward the conserved nucleoprotein of the virus. Different or repeating epitopes of the A or B nucleoprotein are recognized by the antibodies (usually monoclonal) used in assay systems. In one example, an anti-Flu A antibody targeting a repeating nucleoprotein epitope is used as the mobile labeling reagent and capture reagent. The Flu B detection portion of the assay is composed of a monoclonal antibody targeted against a specific portion of the influenza B nucleoprotein as the mobile labeling reagent, with a different monoclonal anti-Flu B antibody (recognizing a different portion of the influenza B nucleoprotein) immobilized as a capture reagent. Anti-influenza A and B monoclonal antibodies are available from Medix Biochemica (Kauniainen, Finland), Fitzgerald Industries, International (Concord, Mass.) and Chemicon (Temecula, Calif.).

In the case of an assay system for the detection of *Streptoccocus* (Strep) A, a polyclonal antibody (for example, Rabbit anti-Strep A) targeting a repeating carbohydrate antigen is used as the mobile labeling reagent and also in the capture zone. Such polyclonal antibodies are available from a variety of commercial sources, such as Strategic Biosolutions (Newark, Del.).

As used herein, "capture situs," "detection situs," and "capture zone" are used interchangeably. The immobilized capture reagent is bound at the capture situs on the analyte detection membrane. The capture situs may be impregnated throughout the thickness of the membrane in the capture situs (e.g., throughout the thickness of the sheet or strip if the carrier is in this form). Such impregnation can enhance the extent to which the immobilized reagent can capture any analyte or labeled reagent, present in the migrating sample.

Alternately, the immobilized capture reagent is bound only to the surface of the membrane or only impregnates partially the thickness of the membrane.

The results of an analysis conducted using a device according to the invention may be read in the capture zone by noting the presence or absence of a visible signal at the location of the capture situs or zone. For example, a labeling reagent bound to an analyte will bind to the capture zone and concentrate the label such that it is visible. The use of a control is helpful for indicating the time when test results can be read, as described above. Thus, when the expected signal appears at the control situs, the presence or absence of a color in the capture situs can be noted. The use of different colors for test and control regents or labels aids in this process.

Capture reagents may be applied to, for example, the analyte detection membrane via printing, spotting, and like techniques. One skilled in the art having the benefit of this disclosure, would know the appropriate technique for their intended purpose. Optionally, after the application of the capture reagent to the membrane, a blocking agent or agents may be applied or immobilized in situ.

The capture reagent is immobile, i.e., is not affected by the lateral flow of the liquid sample due to the immobilization to the porous material. The particle or molecule of the indicator capture reagent can be natural, or non-natural, i.e., synthetic. Once the indicator capture reagent binds the analyte-mobile labeling reagent(s) complex it prevents the analyte-mobile labeling reagent from continuing with the lateral flow of the liquid sample.

The terms "analyte detection membrane," "analyte detection region," and "analyte detection situs," as used herein, refer to the portion of the assay device which is in lateral flow contact with the absorbent sink, and either the porous material of the sample receiving membrane and/or the porous material of the conjugate forming membrane or region. The contact between the membranes can be an overlap, stacked or end-to-end contact or any other configuration that allows flow contact. The analyte in the sample should be capable of migrating through the membranes with lateral flow, e.g. capillary flow, with the liquid sample. The analyte detection membrane may be made of a porous material. Preferably, the analyte detection membrane is made of nitrocellulose. The analyte detection membrane can contain the mobile labeling reagents, the immobile indicator capture reagent and the immobile control capture reagent. In other embodiments, the analyte detection membrane contains only the immobilized control capture reagent and the capture reagent. In certain embodiments, one or more of the analyte detection membrane, sample receiving membrane, mobile labeling reagent membrane, and absorbent sink are made of the same materials and may be made of a single piece of material that contains zones or regions.

Features of the analyte detection membrane include its ability to wick fluids and to bind proteins. Exemplary materials include nitrocellulose, nylon or the like. In a preferred embodiment of this invention, the material is nitrocellulose with or without laminated solid support such as polyester. Nitrocellulose is readily available from numerous suppliers, as discussed above.

The immobilized capture reagent in the capture situs is preferably a highly specific antibody, and more preferably a monoclonal antibody. In one embodiment of the invention involving a sandwich type reaction, the mobile labeling reagent is also preferably a highly specific antibody, and more preferably a monoclonal antibody.

The "conjugate forming membrane," "conjugate forming region," and "conjugate forming zone" are used interchangeably herein and may have releasably bound thereto an enzyme-antibody conjugate or particulate moieties which may or may not be visible, and which can be detected if accumulated in the capture zone. The visible moieties, as described above, can be dyes or dyed polymers which are visible when present in sufficient quantity, or can be, and are preferred to be particles such as dyed latex beads, liposomes, or metallic, organic, inorganic or dye solutions, for example, carbon black, dyed or colored cells or organisms, red blood cells and the like. The enzyme-antibody conjugate or particulate moieties used in the assay provide the means for detection of the nature of and quantity of result, and accordingly, their localization in the capture situs or zone may be and is preferably a function of the analyte in the sample. In general, this can be accomplished by coupling the enzyme-antibody conjugate or particulate moieties to a ligand that binds specifically to the analyte, or which competes with analyte for a capture reagent in the capture zone.

In one approach, the conjugate, or particulate moieties are coupled to a specific binding partner that binds the analyte specifically to form, for example a mobile labeling reagent. For example, if the analyte is an antigen, a labeled antibody specific for this antigen may be used or a labeled immunologically reactive fragments of the antibody, such as $Fab'_2$, Fab or Fab' may also be used. These mobile labeling reagents may then bind to an analyte in a sample as the sample passes through the labeling zone or situs and are carried into the capture situs by the liquid flow. When the complex reaches the capture zone or situs, it is captured by an analyte-specific capture reagent, such as an antibody. For example, the labeled antibody is an anti-α hCG antibody and the capture regent is an anti-β hCG antibody. Excess liquid sample may be taken up by the absorbent sink.

In another approach, the conjugate or particulate moieties are coupled to a labeled ligand which is competitive with analyte for a capture reagent in the capture situs, most typically, other molecules of the analyte itself. Both the analyte from the sample and the labeled competitor bound to the conjugate or particulate moieties are then carried into the capture zone. Both analyte and its competitor then react with the capture reagent, which in this instance is also typically specifically reactive with an analyte and its competitor. The unlabeled analyte thus is able to reduce the quantity of competitor-conjugated conjugate or particulate moieties that are retained in the capture zone. This reduction in retention of the conjugate or particulate moieties becomes a measure of the analyte in the sample.

The term "adequate mechanical strength," as used herein, refers to a desired support to the assay device so as to function properly. The adequate mechanical strength is the support achieved for the entire assembled assay device so as to function properly in the collection and analysis of the analyte in the liquid sample. The total thickness of all of the layers of the immunoassay device is preferably at least 0.003 inches thick. The total thickness of the immunoassay device consists of the thickness of the backing, the membrane elements, label pads (if desired), and the cover. This minimum total thickness is desired in order to produce the desired adequate mechanical strength or support for the device to function effectively. Adequate mechanic strength, in the test strip embodiment, may be achieved, for example, by the backing.

The term "plastic material," or "plastic cover," "cover," or "housing" as used herein refers to any plastic material, which can cover the porous material of the device. Preferably, this is Mylar®, however, those skilled in the art will know of various materials that can be used for such purposes. For example, Mylar®, vinyl, other polyesters, polycarbonate, methyl methacrylate polymer, polystyrene, polyethylene, polypropylene, or waxed cardboard. The housing can be one continuous plastic or separate pieces as shown in the figures. The housing allows the discrete control and discrete capture situses to be viewed and allows for sample to be applied to the sample application membrane. Thus, if the cover is clear then the result can be viewed through the clear cover. If the cover is opaque, then a window, aperture, gap or hole is present in the housing so the results can be viewed.

The structure of the test strip with a backing may be a laminate structure with the backing adhered to a back of the test strip to provide adequate mechanical strength to the device, e.g., to provide support and strength characteristics of the porous material and overall device such that lateral flow of liquid through the device will not be interrupted, for instance by the collapse or disintegration of the device upon wetting. Additional support for the device during the immunoassay may be provided by the walls of a test tube against which the device may rest during the lateral flow.

The term "top" refers to the upper surfaces of the membranes of the device, e.g., the top surface of the test strip.

Test strip backing according to the present invention may be made of, for example, mylar, vinyl, polyester, polycarbonate, methyl methacrylate polymer, polystyrene, polyethylene, polypropylene, and waxed cardboard.

Alternatively, the backing may be a molded plastic backing. The backing may have a thickness of between about 0.001 inches to about 0.010 inches. The backing material may have an adhesive on one side so as to attach the porous material or membrane. The structure of the test strip with a backing may be a laminate structure with the backing covering the back of the test strip and providing adequate mechanical strength to the device, e.g., providing support and strength characteristics of the porous material and overall device such that lateral flow of liquid through the device will not be interrupted, for instance by the collapse or disintegration of the device upon wetting.

A method of using the invention includes the steps of applying a sample to an assay device; and observing a result of the assay. The devices described above may be used in the methods.

The devices of the invention may also be packaged individually or with multiple devices. Each device may be used only one time or they may be designed for multiple uses. The devices may also be packaged as a kit with instruction sheets to inform the user on the proper use of the device.

FIG. 1A is a schematic view of one device according to the invention. The device incorporates a porous analyte detection membrane 5, running almost the length of housing 10 and 11. A procedural control 12 is located on a top surface of the interior of the housing 11. The analyte detection membrane 5 is in lateral flow contact with a conjugate forming membrane 15 and sample receiving membrane 20. An interfering agent immobilization zone 28 is located on the conjugate forming membrane 15. The analyte capture situs 24 is also in lateral flow contact with the absorbent sink 25. The sample receiving membrane 20 is located beneath the sample application aperture 30 such that a sample applied through the sample application aperture 30 would be received by the sample receiving membrane 20. The sample would then flow through the conjugate forming membrane and mobilize the mobile labeling reagent contained in, on, releasably immobilized on, or adhered to the conjugate forming membrane. The sample and the mobilized labeling reagent would then pass through the interfering agent immobilization zone 28 where any interfering agents in the sample would be bound by the immobilization zone 28. The housing 10 has, in addition to the sample application aperture 30, an observation window 35 positioned to allow a view of the capture situs, the control situs (240 and 246 of FIG. 2), and a procedural control 12.

FIG. 1B is a schematic of the top of the housing 10 of FIG. 1A. The top of the housing 10 has a sample application aperture 30 and an observation window 35. The observation window may be fitted with a transparent or semi-transparent material that is impervious or semi-impervious to water or it may be an aperture that is not fitted with any materials. Window materials for use in the invention, include, glass, polypropylene, and the like. A person skilled in the art would be able to determine proper window materials for a particular purpose having the benefit of this disclosure.

FIG. 1C is an alternate embodiment of a device according to the invention. The device incorporates a porous analyte detection membrane 150, running almost the length of housing 110 and 111. A procedural control 112 is located on a bottom surface of the analyte detection membrane 150. The analyte detection membrane 150 is in lateral flow contact with a conjugate forming membrane 115 and sample receiving membrane 120. Interfering agent immobilization zones 128 and 129 are located on the conjugate forming membrane 115. The analyte capture situs 124 is also in lateral flow contact wit the absorbent sink 125. The sample receiving membrane 120 is located beneath the sample application aperture 130 such that a sample applied through the sample application aperture 130 would be received by the sample receiving membrane 120. The sample would then flow through the conjugate forming membrane and mobilize the mobile labeling reagent contained in, on, releasably immobilized on, or adhered to the conjugate forming membrane. The sample and the mobilized labeling reagent would then pass through the interfering agent immobilization zones 128 and 129 where any interfering agents in the sample would be bound by the immobilization zones 128 and 129. The housing 110 has, in addition to the sample application aperture 130, an observation window 135 positioned to allow a view of the capture situs, the control situs (240 and 246 of FIG. 2), andaprocedural control 112.

Referring to FIG. 2, a top view of the lateral flow membranes according to one embodiment of the invention is shown. A sample receiving membrane 220 is in lateral flow contact with a conjugate forming membrane 215, an analyte detection membrane205, and an absorbent sink 225. The conjugate forming membrane 215 has releasablybound to it a mobile labeling reagent 216 that will be mobilized when in contact with afluid. The analyte detection membrane 205 has an immobilized interfering agent immobilization zone 206 bound thereto, as well as an immobilized capture reagent 240 ata capture situs 241 and a control reagent 245 at a control situs 246.

Figure 3:
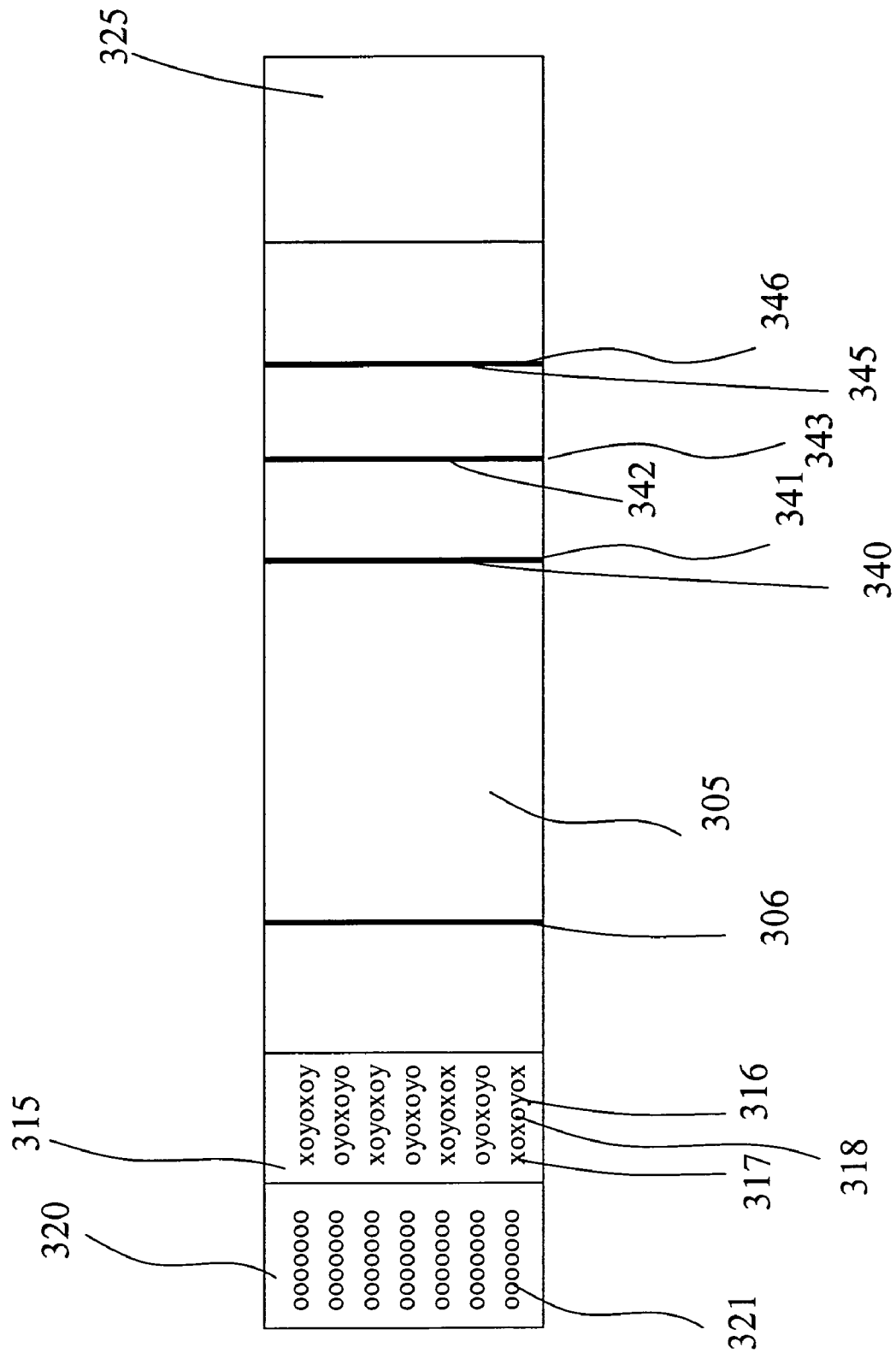
FIG. 3 depicts a top view of a device according to the invention.

FIG. 3 illustrates another embodiment of the invention. A top view of the lateralflow membrane according to another embodiment of the invention is shown. A samplereceiving membrane 320 is in lateral flow contact with a conjugate forming membrane 315, an analyte detection membrane 305, and an absorbent sink 325. The sample receiving membrane 320 has bound thereto an interfering agent immobilization agent 321. The conjugate forming membrane 315 has releasably bound to it two mobile labeling reagents 316 and 317 that will be mobilized when in contact with a fluid. Each mobile labeling reagent is specific for a different analyte. The conjugate forming membrane 315 has an immobilized interfering agent immobilization zone 318 bound to immobilize interfering agents from a sample. The analyte detection membrane 305 also has an immobilized interfering agent immobilization zone 306 bound thereto. The analyte detection membrane 305 has two immobilized capture reagents 340 and 342 at capture situs 341 and capture situs 343, respectively. The capture reagents are specific for one or the other of the mobile labeling reagents when bound to an analyte. There is also an immobilized control reagent 345 at a control situs 346 to serve as a control that the assay is functioning.

Figure 4:
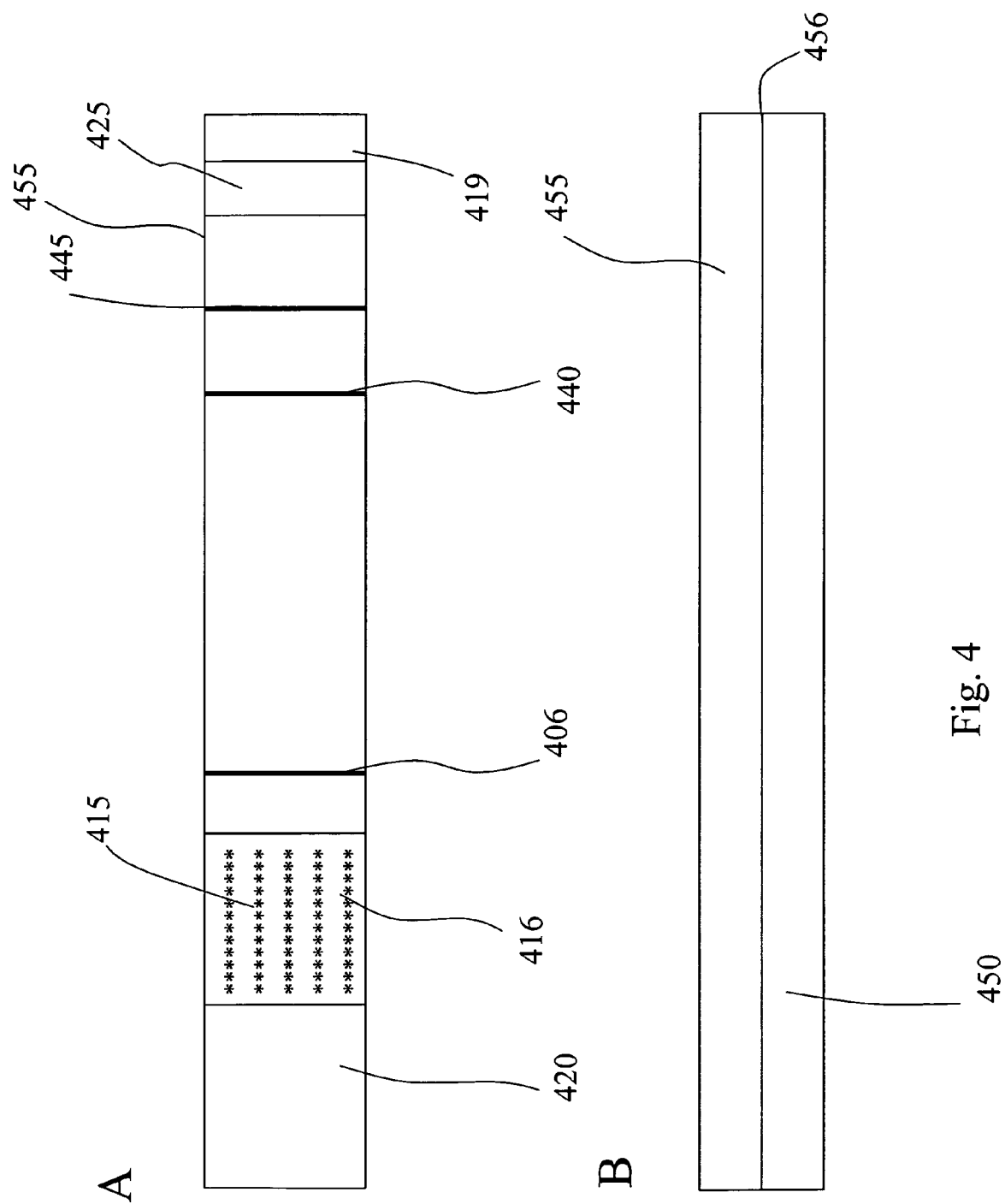
FIG. 4A depicts a top schematic view of a device according to the invention.
FIG. 4B depicts a side view of a device according to the invention.

FIG. 4 depicts a further embodiment of the invention suitable for use as a dipsitck wherein the sample to be analyzed is introduced to the lateral flow apparatus by dipping the device into the sample or by flowing the sample over the sample receiving zone of the device. Referring to FIG. 4, the test strip 455 has a grip zone 419 to allow handling of the test strip and a sample application zone 420, which is in lateral flow contact with the conjugate forming region 415 containing a labeled specific binding reagent 416. The sample receiving zone is also in flow contact with the absorbent sink 425. The absorbent sink is covered with a covering, for example a plastic film. The film covered absorbent sink. The film covered absorbent sink may be a grip zone or may be in addition to grip zone 419 as shown. On the test strip 455 and distal to the conjugate forming region 415 is the immobilized interfering agent immobilization zone 406. Distal to the interfering agent immobilization zone 406 is the capture situs 440 and the control situs 445. Immobilized on the test strip at the capture situs 440 is a capture reagent. The test strip is backed by backing 450 on the bottom surface 456 of the assay strip 455.

In operation, the sample application zone 420 may be exposed to an aqueous sample, e.g., by dipping the end of the test strip into a sample or by applying a sample to the end of the test strip with a sample applicator. The liquid sample will then permeate the length of test strip 455, for example, by capillary flow. The sample will mobilize the mobile labeling reagent 416 from the conjugate forming region 415 and can bind to an analyte if present in the sample. The fluid will then continue permeating the test strip and pass through the immobilized interfering agent immobilization zone 406. Interfering agents in the sample, either bound to the mobile labeling reagent or free interfering agent, may bind to the immobilized interfering agent immobilization zone elements. As the sample continues to permeate the test strip it then travels through the capture situs 440 and the control situs 445. At the capture situs, any analyte bound to mobile labeling reagent may bind to the capture reagent to be detected, for example, through a "sandwich" reaction involving an analyte in the sample. Any unbound mobile labeling reagent will pass through the capture situs and may be bound at the control situs 445 by the control reagent.

Figure 5:
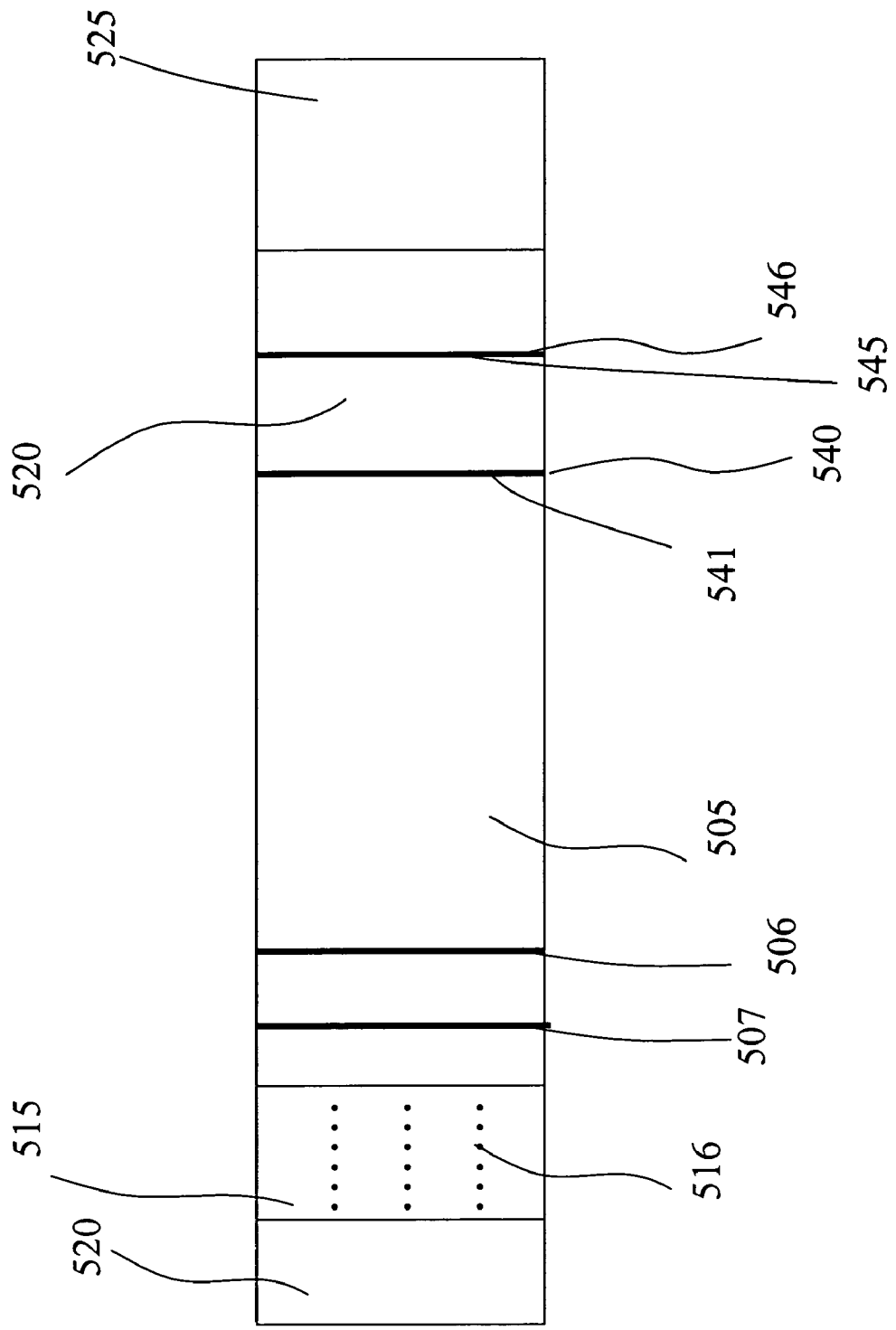
FIG. 5 depicts a top view of a devise according to the invention.

FIG. 5 in an alternate embodiment of a device according to the invention. A top view of the lateral flow membranes according to one embodiment of the invention is shown. A sample receiving membrane 520 is in lateral flow contact with a conjugate forming membrane 515, an analyte detection membrane 505, and an absorbent sink 525. The conjugate forming membrane 515 has releasably bound to it a mobile labeling reagent 516 that will be mobilized when in contact with a fluid. The analyte detection membrane 505 has an immobilized interfering agent immobilization zones 506 and 507 bound thereto, as well as an immobilized capture reagent 540 at a capture situs 541 and a control reagent 545 at a control situs 546.

Many circumstances may affect the absolute reactivity of lateral flow assays, including, but not limited to, manufacturing-derived variations, operator induced variations, environmentally induced variations and sample effects. With conventional lateral flow assays, any of these variations may act to repress or arguably enhance reactivity of one strip over another, resulting in possible false negative or false positive results. Not controlling for these or other variations may result in significant imprecision, non-reproducibility, lack of sensitivity and lack of specificity of the tests.

Lateral flow assays are also subject to a number of interferences that might affect the absolute amount of binding of either analyte binding agent or control agent to the test zones. Influencing factors may include: 1) variability in the release of the second analyte binding agent or the control agent from a conjugate pad, 2) device to device variation in non-specific binding, 3) variability in the movement of the analyte binding population through or along the test strip during the assay due to variation in the pore size of the test strip or porous material of either the sample receiving membrane or the analyte detection membrane materials or non-specific aggregation of the analyte binding agent, or 4) binding of interfering agents. The devices of the invention solve the sample effects due to interfering agents that lead to false positive or false negative results.

Such devices can be provided as kits suitable for home use, comprising a plurality (e.g. two) of devices individually wrapped in moisture impervious wrapping and packaged together with appropriate instructions to the user.

Kits of dipstick embodiments may include a plurality of devices, for example, more than one device, e.g., 10, 25, 100, or 150 devices may be packaged together with instructions for use. Instructions for use may include testing procedures, interpretation procedures, performance characteristics, and information on the test device.

Kit of devices enclosed in housing according to the invention may be packaged with one or more devices, for example, 5, 10, 25 or 30 or more devices may be packaged and sold together with instructions for use. Optional other materials provided in the kit may include an control set with negative, positive controls. The instructions may contain information on storage and handling of the devices after purchase and information in the testing procedures.

Kits may include, for example:

25 Test Sticks in a container;
25 Test Tubes;
25 Transfer Pipettes;
25 Capillary Tubes with 1 Capillary Bulb;
1 Diluent (contains buffer with 0.2% sodium azide);
1 Mono Positive Control (contains rabbit anti-beef stroma in tris buffer with 0.2% sodium azide; and
0.05% gentamycin sulfate preservatives);
1 Mono Negative Control (contains goat albumin in tris buffer with 0.2% sodium azide);
1 Work Station; and
1 Directional Insert Other features and advantages of the invention will be apparent from the following detailed description of the presently preferred embodiments of the invention in conjunction with the accompanying drawings and from the claims.

EXAMPLES

It should be appreciated that the invention should not be construed to be limited to the examples, which are now described; rather, the invention should be construed to include any and all applications provided herein and all equivalent variations within the skill of the ordinary artisan.

Example 1

Influenza Test Device

When testing for the presence of Influenza A and/or B, some subjects have a known tendency to produce the false positive result, especially under "stress conditions," i.e., "stress conditions" refers to extracting multiple negative samples in the same solution to produce a very concentrated solution of the interfering substance. The interfering substance is presumed to have the ability to bind mouse monoclonal antibodies so that a monoclonal conjugated to colloidal gold can interact with the analyte of interest and the first monoclonal antibody test line link together to give the appearance of a positive result. A "control line" is positioned after the test line with regard to the flow path of the sample through the various zones. The control line uses an "anti-mouse" to capture mobile labeling reagent that had not bound to the capture reagent. Mouse IgG competes with the conjugated antibody for binding and the net result is a reduction in control line signal intensity.

In a device of the invention, a mouse IgG was used as an interfering agent immobilization zone, which did not interfere at a Goat anti-mouse IgG control line. Mouse IgG was immobilized on a line or multiple lines in advance of the immobile capture reagent. The interfering substance(s) in the sample that might otherwise have bound the mobile labeling reagent bound to the immobilized first situs and was removed and did not reach the capture reagent. This approach prevented the formation of a false positive result. Because the immobilization zone mouse IgG was bound to the membrane, the reduction in control line intensity that would be seen with the use of free mouse IgG in the sample treatment zone or conjugate zone is not noted. This improved the test accuracy as well as the test scoring of positive results.

A solution of a solubilized extract from a patient sample was applied to a test device of the invention where it contacted the sample receiving membrane. The sample receiving membrane conditioned the sample prior to the continued flow of the sample to the conjugate forming membrane. In the conjugate forming membane, the liquid from the sample rehydrated the conjugate which was composed of a colloidal gold particle coupled with Mouse monoclonal antibody specific for Influenza A (Flu A) or Influenza B (Flu B) antigens. If Flu A or Flu B is present in the extracted sample, it bound to the specific gold conjugate. Any interfering substances in a patient sample (which could include anti-mouse antibodies) may recognize the antibodies on the colloidal gold and bind to the conjugate particles. In all cases, the solubilized gold conjugates were carried along the path of the printed nitrocellulose membrane. A zone, situs or line of Mouse IgG was immobilized on the membrane to form a first situs. If an interfering substance specific for Mouse IgG bound to the gold conjugates, it may also be bound and essentially captured at the first situs. This serves as a immobilization zone and prevents subsequent binding to the first capture situs, (which in this example is a mouse IgG against Flu A). If the interfering agent-mobile labeling reagent complex bound to the capture reagent, it could be interpreted as a false positive. The immobilization zone of this complex prevents the false positive result. The plastic casing covered the location of the Mouse IgG line so that these are not visible to the user if binding does occur. If detectable Flu A or Flu B antigen is present, the antigen is captured at the specific capture situs. Since another portion of the antigen is bound to the specific gold conjugate, a "sandwich" is formed, and the appropriate test line becomes visible. Conjugate that is not captured at the test line continues to flow to the control situs portion of the membrane. In this membrane, immobilized goat-anti Mouse IgG captures the portion of the antibodies coupled to the gold and a visible line appears. Liquid continues to flow to the absorbent sink, which acts as a reservoir at the end of the test strip.

Example 2

Urine Testing:

Samples from 158 women of child-bearing age were collected and evaluated within 72 hours of collection. Testing of these samples with the assay device produced according to the invention produced the expected result. The presence of the immobilization zone did not interfere with the assay result.

Serum Testing:

Two-hundred characterized serum samples were evaluated, eleven of which produced false positive results with a different assay device that did not have the interfering agent immobilization zone. None of the eleven samples produced a false positive result when assayed with an assay device according to the invention.

Heterophilic antibodies (IgM and IgG mediated) are known to produce false positive results in immunometric assays. To combat the false positive results in an hCG assay for urine, serum, or blood, an IgG blocking agent was immobilized on a membrane as an interfering agent immobilization zone to remove the heterophilic antibodies from the sample. The urine or serum solutions described above were individually applied to an assay device cassette where they came into contact with a sample receiving membrane. The sample then flowed though the sample receiving membrane to the analyte detection membrane where the sample rehydrated the mobile labeling reagent, a charcoal particle coupled to an F(ab)'2 mouse monoclonal antibody specific for beta-hCG. If hCG is present in the sample, it will bind to the mobile labeling reagent. If an interfering agent is present in the sample, it may also bind to the mobile labeling reagent. The sample then flowed down the membrane and encountered the interfering agent immobilization zone. The immobilization zone bound to interfering agent bound to the mobile labeling reagent. The interfering agent immobilization zone was Mouse IgG immobilized on the membrane. This serves as a immobilization zone and prevents subsequent binding of the interfering agent-mobile labeling reagent complex to the capture reagent and prevents a false positive result. The sample continues to flow, and if hCG is present, the alpha subunit is captured by the anti-alpha-hCG antibody immobilized at the capture situs. The beta-hCG subunit is bound by the mobile labeling reagent and will produce a visible signal that may be visualized to determine the assay results. Mobile labeling reagent not captured at the capture reagent continues to flow with the sample and is captured by the control reagent at the control situs. The capture reagent is an immobilized goat-anti Mouse IgG. The sample continues to flow through the membranes to the absorbent sink, which acts as a reservoir for the liquid.

After completion of the assay, the device was dismantled and the presence of a visible line at the site of the interfering agent immobilization zone was detected in samples that previously gave false positive results in other assays. This demonstrated that the interfering agent immobilization zone was binding to the mobile labeling reagent bound to an interfering agent.

While the invention has been disclosed with reference to specific embodiments, it is apparent that other embodiments and variations of the invention may be devised by others skilled in the art without departing from the true spirit and scope of the invention. The appended claims are intended to be construed to include all such embodiments and equivalent variations.

What is claimed is:

1. An assay device for detection of the presence or absence of an analyte in a sample comprising:
   (a) a sample receiving membrane which conducts flow of a sample, and in flow contact with,
   (b) an analyte detection membrane which conducts flow of the sample comprising an interfering agent immobilization zone at a first situs, a conjugate forming membrane comprising a mobile labeling reagent at a labeling situs located upstream of the interfering agent immobilization zone, and an immobile capture reagent at a capture situs, wherein the labeling reagent is capable of forming a complex with an analyte and an interfering agent, the capture reagent is capable of binding an analyte-labeling reagent complex, and the interfering agent immobilization zone includes a reagent associated therewith that is capable of binding an interfering agent in the sample.

2. The assay device of claim 1, wherein the flow contact between the sample receiving membrane and analyte detection membrane is lateral flow contact.

3. The assay device of claim 1, wherein the reagent of the interfering agent immobilization zone is adapted to immobilize the interfering agent thereon and the interfering agent is labeled at the labeling situs.

4. The assay device of claim 1, wherein the first situs is located between the sample receiving membrane and the capture situs.

5. The assay device of claim 1, wherein the reagent of the interfering agent immobilization zone adapted to include the interfering agent immobilized thereon.

6. The assay device of claim 1, wherein the assay device is capable of detecting an analyte in a sample selected from the group comprising, blood, serum, nasal fluid, urine, sweat, plasma, semen, cerebrospinal fluid, tears, pus, amniotic fluid, saliva, lung aspirate, gastrointestinal contents, vaginal discharge, urethral discharge, chorionic villi specimens, skin epithelials, genitalia epithelials, gum epithelials, throat epithelials, hair, or sputum.

7. The assay device of claim 1, wherein the sample receiving membrane and theanalyte detection membrane are enclosed in a housing.

8. The assay device of claim 1 wherein, the assay device includes a housing that comprises a sample application aperture and an observation window positioned to display the capture situs.

9. The assay device of claim 1, further comprising an absorbent sink in lateral flow contact with the analyte detection membrane.

10. The assay device of claim 1, wherein the assay device further includes a control reagent immobilized at a control situs on the assay device.

11. The assay device of claim 10, wherein the control reagent comprises an antimouse lgG, an anti-goat rgG, an anti-cow lgG, anti-rabbit lgG, or an anti-rat lgG.

12. The assay device of claim 10, wherein the, control reagent is immobilized between the immobile capture reagent and, an end of the analyte detection membrane.

13. The assay device of claim 1, wherein the assay device is configured such that an accumulation of the interfering agent at the interfering agent immobilization zone does not produce a signal indicative of the presence of interfering agent in the sample.

14. The assay device of claim 1, wherein the assay device is capable of detecing an analyte selected from the group comprising a protein, peptide; small molecule; antibody, nucleic acid, viruse, virus particle, human chorionic gonadotrophin, luteinizing hormone, estrone-3glucoronide, pregnanediol-3-glucoronide, insulin, glucagon, relaxin, thyrotropin, somatotropin, gonadotropin, follicle-stimulating hormone, gastrin, bradykinin, vasopressin, polysaccharides, estrone, estradiol, cortisol, testosterone, progesterone, chenodeoxycholic acid, digoxin,. cholic acid, digitoxin, deoxycholic acid, lithocholic acids; vitamins, thyroxine, triiodothyronine, histamine, serotorin, prostaglandin, drug, drug metabolite, ferritin, or CEA.

15. The assay device of claim 1, wherein the interfering agent is an antibody or an analyte mimic.

16. The assay device of claim 1, wherein an accumulation of the interfering agent and reagent at the interfering agent immobilization zone produces a signal indicative of the presence of interfering agent in the sample.

17. An assay device for detection of the presence or absence of an analyte in a sample comprising:
   (a) a sample receiving membrane which conducts flow of a liquid sample, in flow contact with;
   (b) an analyte detection membrane which conducts flow of the sample comprising an interfering agent immobilization zone at a first situs, a conjugate forming membrane comprising a mobile labeling reagent at a labeling situs, and an immobile capture reagent at a capture situs, wherein the labeling reagent is movable along the membrane and the labeling reagent is capable of forming a complex with an analyte and the interfering agent, the capture reagent is capable of binding an analyte-labeling reagent complex, and the interfering agent immobilization zone includes a reagent associated therewith that is capable of binding an interfering agent-labeling reagent complex thereto; and
   (c) an absorbent sink in flow contact with the analyte detection membrane.

18. An assay device for detection of the presence or absence of an analyte in a sample comprising:
   (a) an elongate membrane having, a sample receiving area, a conjugate forming area and an analyte detection area which conductthe flow of a sample therealong, and
   (b) an analyte detection area which conducts flow of the sample comprising an interfering agent immobilization zone at a first situs, a conjugate forming area comprising a mobile labeling reagent at a labeling situs located upstream of the interfering agent immobilization zone, and an immobile capture reagent at a capture situs, wherein the labeling reagent is capable of forming.a complex with an analyte and an interfering agent, the capture reagent is capable of binding an analyte-labeling reagent complex, and the interfering agent immobilization zone includes a reagent associated therewith that is capable of binding an interfering agent in the sample.

* * * * *